United States Patent
Heiman

(10) Patent No.: US 10,350,348 B2
(45) Date of Patent: Jul. 16, 2019

(54) MANUALLY ACTUATED INFUSION DEVICE WITH DISPLAY

(71) Applicant: ANIMAS CORPORATION, West Chester, PA (US)

(72) Inventor: Stephen Heiman, West Chester, PA (US)

(73) Assignee: LifeScan IP Holdings, LLC, Malvern, PA (US)

( * ) Notice: Subject to any disclaimer, the term of this patent is extended or adjusted under 35 U.S.C. 154(b) by 180 days.

(21) Appl. No.: 15/161,387

(22) Filed: May 23, 2016

(65) Prior Publication Data

US 2017/0333622 A1 Nov. 23, 2017

(51) Int. Cl.
| | |
|---|---|
| *A61M 5/142* | (2006.01) |
| *A61M 5/145* | (2006.01) |
| *A61M 5/31* | (2006.01) |
| *A61M 5/315* | (2006.01) |

(52) U.S. Cl.
CPC ........ *A61M 5/1424* (2013.01); *A61M 5/1452* (2013.01); *A61M 5/1456* (2013.01); *A61M 5/14248* (2013.01); *A61M 5/3148* (2013.01); *A61M 5/14566* (2013.01); *A61M 5/31568* (2013.01); *A61M 2005/14268* (2013.01); *A61M 2005/3126* (2013.01); *A61M 2205/3306* (2013.01); *A61M 2205/581* (2013.01); *A61M 2205/582* (2013.01); *A61M 2205/583* (2013.01); *A61M 2205/8206* (2013.01); *A61M 2209/04* (2013.01)

(58) Field of Classification Search
CPC ............ A61M 5/1424; A61M 5/14244; A61M 5/14248; A61M 5/1452; A61M 5/1456; A61M 2005/14268; A61M 2005/14573; A61M 2005/8206
See application file for complete search history.

(56) References Cited

U.S. PATENT DOCUMENTS

| | | |
|---|---|---|
| 4,300,554 A | 11/1981 | Hessberg et al. |
| 6,585,698 B1 | 7/2003 | Packman et al. |
| 6,599,272 B1 | 7/2003 | Hjertman et al. |
| 7,678,084 B2 | 3/2010 | Judson et al. |
| 8,062,268 B2 | 11/2011 | Ratjen |
| 8,361,036 B2 | 1/2013 | Moller et al. |
| 8,465,460 B2 | 6/2013 | Yodfat et al. |

(Continued)

FOREIGN PATENT DOCUMENTS

| | | |
|---|---|---|
| WO | 2013098421 A1 | 7/2013 |
| WO | 2015007813 A1 | 1/2015 |

(Continued)

OTHER PUBLICATIONS

International Search Report and Written Opinion issued in related International Patent Application No. PCT/US2017/033747, dated May 8, 2018, 14 pages.

*Primary Examiner* — Bhisma Mehta
*Assistant Examiner* — James D Ponton

(57) ABSTRACT

A manually operated medicament infusion device is provided. The device is capable of delivering an accurately controlled volume of medicament with reliability. Additionally, the device includes a battery-operated indication device for tracking the number of doses of medication delivered. Optionally, the device includes a ratchet and pawl to prevent inadvertent dispensing of medicament.

4 Claims, 11 Drawing Sheets

(56) References Cited

U.S. PATENT DOCUMENTS

| | | |
|---|---|---|
| 8,556,847 B2 | 10/2013 | Kohlbrenner et al. |
| 9,028,454 B2 | 5/2015 | Veasey et al. |
| 9,220,845 B2* | 12/2015 | Atterbury ......... A61M 5/31566 |
| 2002/0151855 A1 | 10/2002 | Douglas et al. |
| 2003/0009133 A1* | 1/2003 | Ramey ................ A61M 5/1456 |
| | | 604/155 |
| 2004/0260303 A1 | 12/2004 | Carrison |
| 2006/0069355 A1 | 3/2006 | Judson et al. |
| 2008/0033369 A1 | 2/2008 | Kohlbrenner et al. |
| 2009/0062748 A1* | 3/2009 | Moller ............... A61M 5/31511 |
| | | 604/211 |
| 2010/0081993 A1 | 4/2010 | O'Connor |
| 2010/0292651 A1* | 11/2010 | Yodfat ................ A61M 5/1413 |
| | | 604/189 |
| 2011/0319861 A1 | 12/2011 | Wilk |
| 2012/0004620 A1 | 1/2012 | Spool et al. |
| 2012/0204662 A1 | 8/2012 | Matthias et al. |
| 2012/0330228 A1* | 12/2012 | Day .................. A61M 5/14244 |
| | | 604/82 |
| 2013/0079727 A1 | 3/2013 | Schildt et al. |
| 2014/0074041 A1 | 3/2014 | Pedersen et al. |
| 2014/0163521 A1 | 6/2014 | O'Connor |
| 2014/0312074 A1 | 10/2014 | Madsen et al. |
| 2014/0378903 A1 | 12/2014 | Quinlan |
| 2015/0005703 A1 | 1/2015 | Hutchinson et al. |
| 2015/0314068 A1* | 11/2015 | Alderete, Jr. ..... A61M 5/14244 |
| | | 604/500 |

FOREIGN PATENT DOCUMENTS

| | | |
|---|---|---|
| WO | 2015074977 A2 | 5/2015 |
| WO | 2015144606 A1 | 10/2015 |

* cited by examiner

MANUALLY ACTUATED INFUSION DEVICE WITH DISPLAY

FIELD OF THE INVENTION

The present invention relates to infusion devices. More particularly, the invention relates to manual infusion devices that enable liquid medicaments to be conveniently and safely self-administered by a patient. The pump of the invention includes an indication device suitable for displaying dose information to the pump user.

BACKGROUND OF THE INVENTION

Self-delivery of medicaments by patients dealing with temporary or chronic disease states has been enabled by use of portable, external infusion pumps. Use of these pumps has been shown to improve the quality of life as well as the general health of these patients. However, the size, cost, and complexity of these infusion pumps can be a drawbacks for the users. For example, some of the pumps are electronically controlled and must be programmed to supply the desired amounts of medicaments. This prevents many users from accepting the use of this technology.

Hence, there is a need in the art for a convenient form of treatment using infusion pumps that do not require significant programming or technical skills to use. Preferably, such a treatment would be carried out by an infusion device that is simple to use and mechanically driven. It would also be preferable if the infusion device could be directly attached to the body and not require any electronics to program the delivery rates. The medicament would be preferably delivered through a small, thin-walled tubing or cannula through the skin similar to known technologies.

Although the idea of such a simple delivery device is compelling, many obstacles must be overcome before such a device may become a practical realty. One problem resides in medicament supply. Patients vary greatly on the amount of medicament such a device must carry to provide treatment over a fixed time period of, for example, three days. This is one environment where one size does not fit all. Still further, such devices must be safely wearable and not subject to possible accidental dosing. Still further, such devices must be capable of delivering an accurately controlled volume of medicament with reliability. Finally, a device that provides a means for tracking the number of doses of medication delivered is highly desirable to permit a patient or healthcare provider to ensure that the correct amount of medication is administered over a given period of time. It would be further preferred if the cost of manufacturing such a device would be economical enough so as to render the device disposable after use. As will be seen subsequently, the devices and methods described herein address these and other issues.

DETAILED DESCRIPTION OF THE INVENTION

Figure 1:
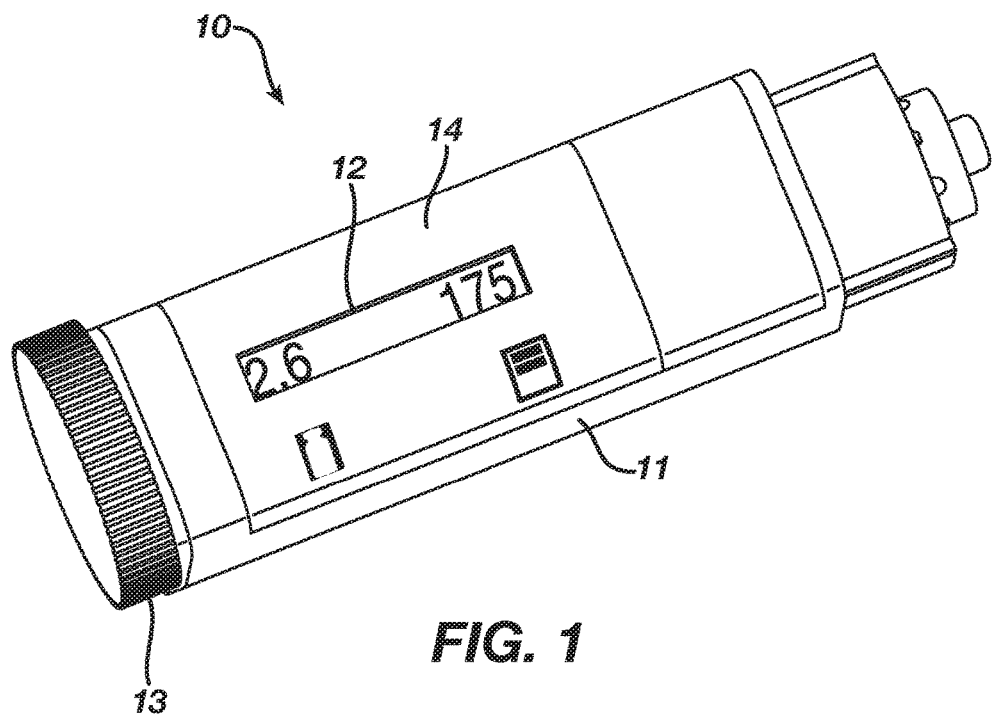
FIG. 1 is a top perspective view of the device of the invention.
Figure 2:
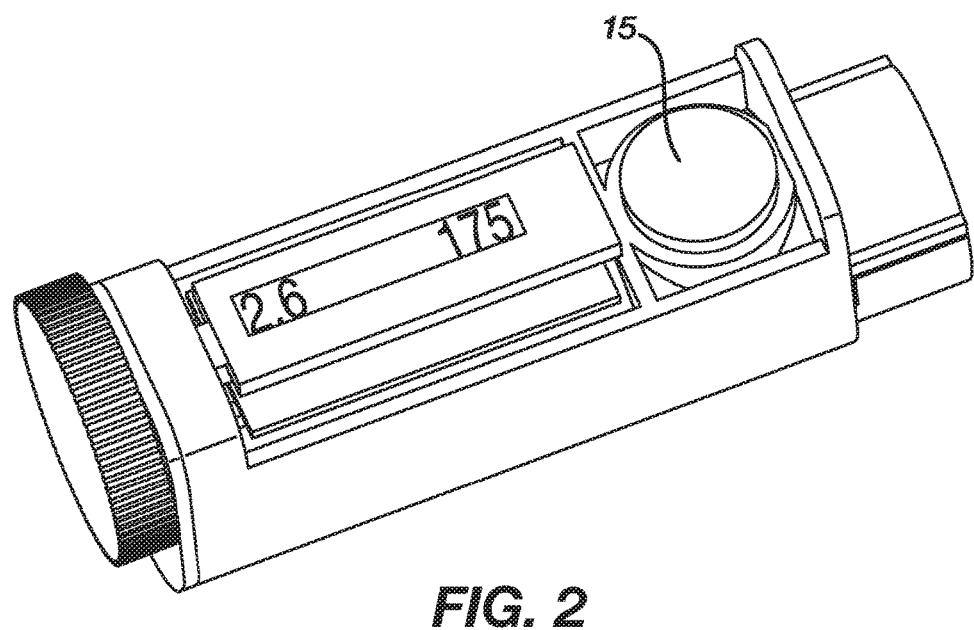
FIG. 2 is a top perspective view of the device of FIG. 1 with a portion of the housing removed.

Referring now to FIG. 1, a top perspective view of a first infusion device embodying certain aspects of the present invention is shown. The device 10 generally includes housing 11, which housing includes indication device 12 within an opening in the housing. Drive wheel 13 is also shown. Indication device 12, as shown, is a display that provides information regarding the medicament doses delivered by, and doses remaining in, device 10. The display may depict numbers, words, icons or the like, but preferably is a single line, numerical display. Preferably, the display indicates the number of insulin units being delivered (shown in FIG. 1 as "2.6") by the device 10 and the number of medicament units remaining (shown in FIG. 1 as "175") within the device to be delivered. The indication device may be any known type of display such as an LCD, LED, OLED, but preferably is an OLED display. As shown in FIG. 2, a power source, such as a coin cell battery 15, is provided within the device, which battery powers the display, as well as the sensors, microcontroller and associated circuits of the device described hereinbelow. Removable housing panel 14 of housing 11 shown in FIG. 1, provides access to the battery. Because the pumping mechanism of the infusion device of the invention is manually operated, the power required for the device is minimal.

Figure 5:
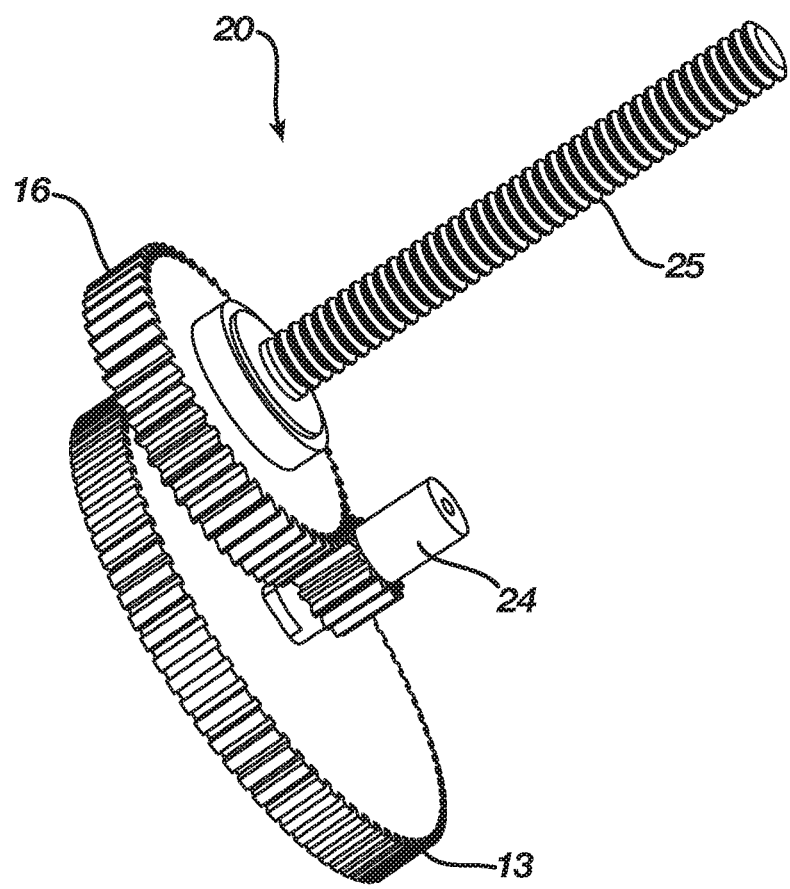
FIG. 5 is a side perspective view of gearing mechanism for the device of FIG. 1.

The infusion device of the invention includes a gearing mechanism that is manually operated. As shown in FIG. 5, in one embodiment, gearing mechanism 20 includes drive wheel 13 with gear 24 extending from a surface thereof. Although a drive wheel is shown, it will be understood that other simple, hand-operated components, capable of providing rotary motion may be used in place of the drive wheel. Gear 24 is designed to mesh with the threads, or gear teeth, of leadscrew base 16, the rotation of which base turns threaded leadscrew shaft 25. Rotation of drive wheel 13 correlates to leadscrew shaft 25 rotation via the enmeshment or gearing interaction of gear 24 with leadscrew base 16. As shown in FIGS. 3, 4, 6 and 7, piston 17 with piston end 18 is movably affixed to leadscrew shaft 25. As leadscrew shaft 25 is rotated by the gearing interaction of gear 24 with leadscrew base 16, piston 17 indexes away (described in further detail hereinbelow), meaning moves farther in distance in a longitudinal direction away from leadscrew base 16 and along leadscrew shaft 25.

For delivery of medicament from the infusion device, small, precise movements of the leadscrew mechanism are desired. The amount of forward movement, or extension, of piston 17 may be directly calculated from the leadscrew pitch. By way of example, the leadscrew may be a #2-56 screw having 56 threads per inch and a gear ratio between the leadscrew base and threaded shaft may be a 4:1 ratio. In this case, one complete turn of drive wheel 13 correlates to a ¼ turn of leadscrew base 16 and a 0.0045 inch extension of piston 17. Pressure from the forward movement of piston end 18 drives a plunger in a medicament cartridge. Thus, if the volume of a medicament cartridge, into which the shaft 25 drives piston end 18, is 0.44 units, this movement would result in infusion of 0.00070 cubic inches (0.11 ml; 1.1. units) of medicament to the user.

Figure 3:
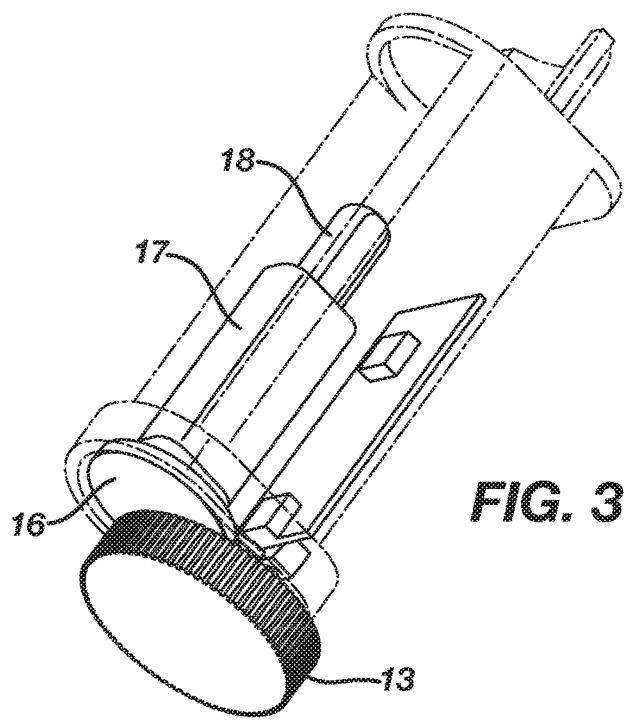
FIG. 3 is a side perspective view of the device of FIG. 1 with a the housing represented by the dotted line with internal components of the device shown.
Figure 4:
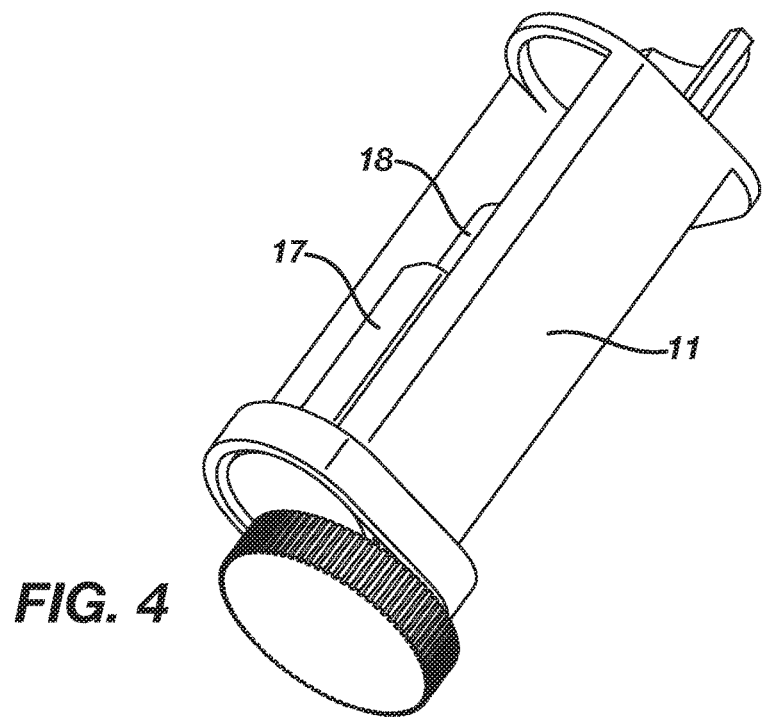
FIG. 4 is a side perspective view of the device of FIG. 1 with a portion of the housing removed.
Figure 6:
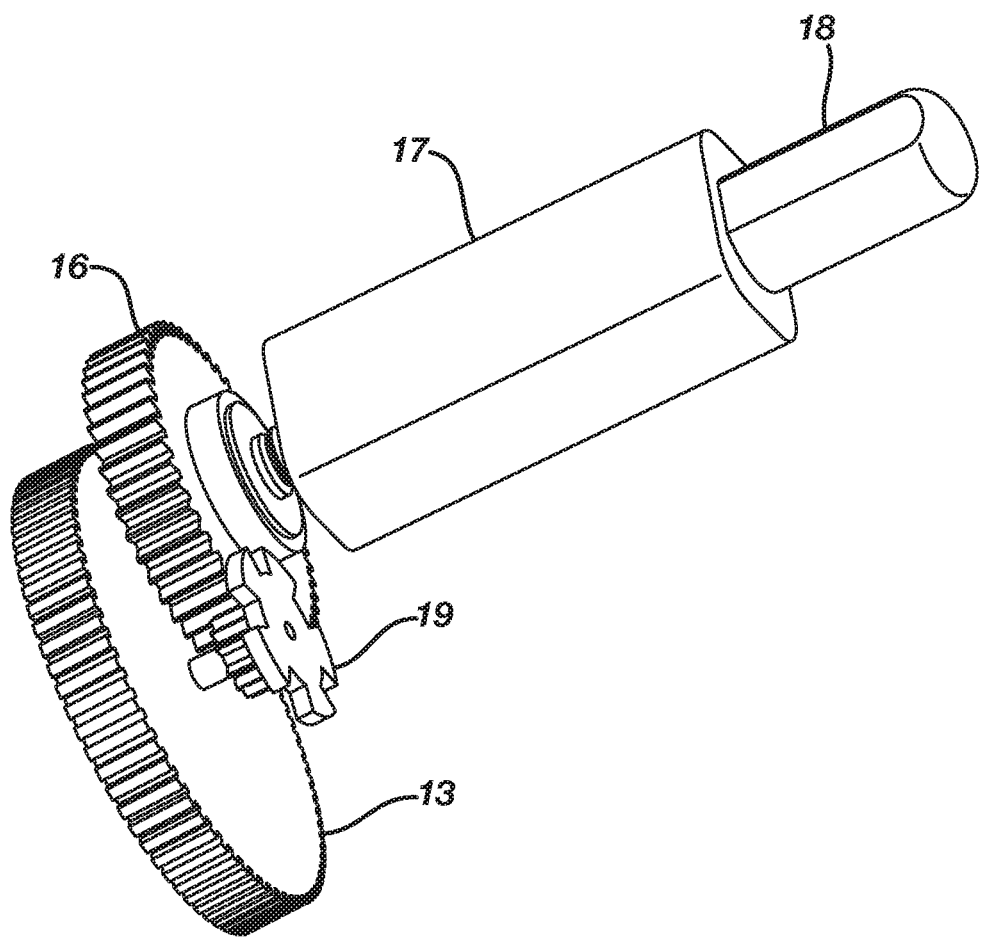
FIG. 6 is a side perspective view of the gearing mechanism of FIG. 5 with a piston and encoder.
Figure 7:
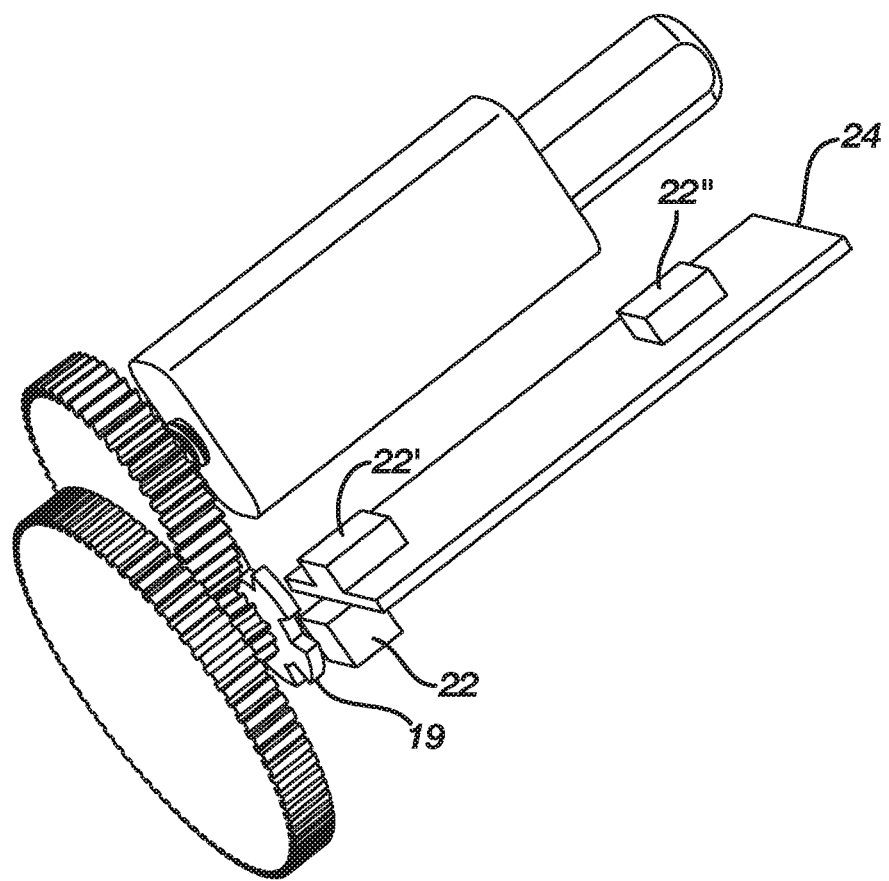
FIG. 7 is a side perspective view of the gearing mechanism, piston, and encoder of FIG. 6 along with optical sensors.

Also included within housing 11 is a sensing mechanism. The sensing mechanism may be any known mechanism capable of electrically connecting to indication device 12. As shown in FIGS. 3 and 7, the sensing mechanism includes a circuit board 24 that includes a microcontroller and display driver (not shown). Circuit board 24 also includes at least one sensor 22 affixed thereto. The sensors may be any sensor type, such as optical sensors, capable of measuring movement of the gears and the piston. As shown in FIGS. 6 and 7, a rotary encoder is used that includes rotary wheel 19. Rotary wheel 19 may contain any desired number of slits or transitions for the optical sensors. Light from optical sensor 22, for example, beamed perpendicular to rotary wheel 19 is either reflected back to a receiver in the sensor or passed through the sensor. The disruption in the beam caused by the slits is used by the sensor electronics to convert the light to electrical signals. For example, the wheel shown in FIG. 6 will provide 10 voltage transitions (5 up and 5 down) resulting in emission of 10 signals per wheel revolution. If one revolution is 1.1 units of medicament, the display can depict those units in increments of about 0.1 units of medicament.

Preferably, additionally provided are sensors for measuring the maximum extension and retraction of the piston 17. These sensors, shown as 22' and 22" on circuit board 24 in FIG. 7, indicate when the medicament cartridge is empty or, as described hereinbelow, fully rewound. Piston 17 is made or coated with a reflective material that reflects beamed light back to the sensors. As the piston moves forward along the threaded shaft 25 and past a sensor, the light beam will not be reflected and provides an indication of the position of the piston. In the fully forward position, no reflection from the piston to either sensor 22' or 22" indicates that the piston is fully extended and, thus, has acted on a plunger within the medicament cartridge to empty the cartridge.

Figure 8:
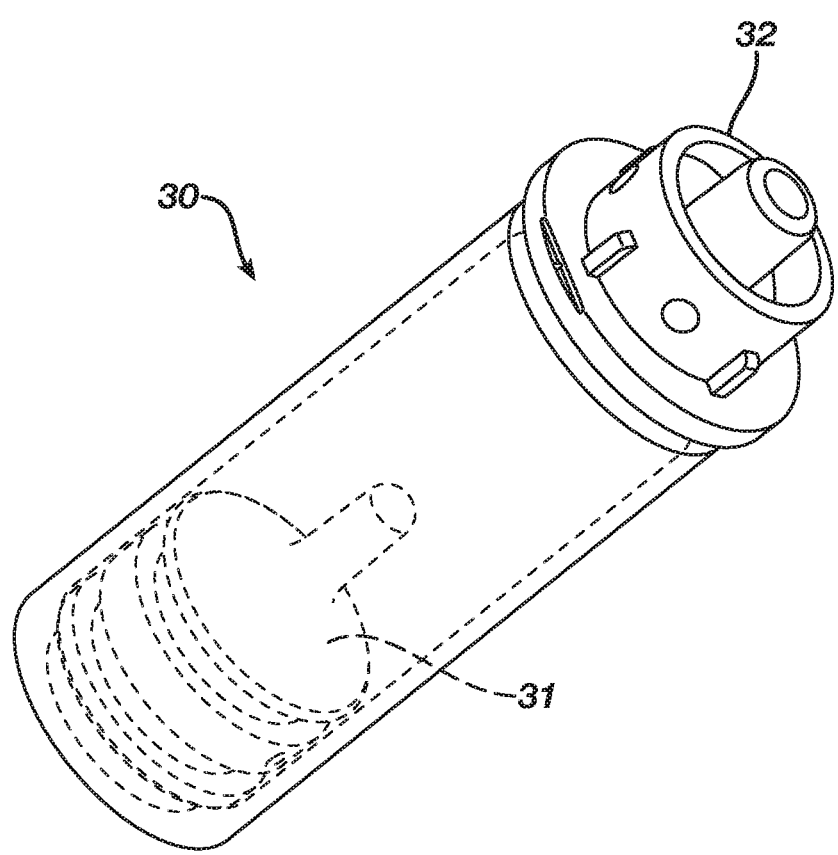
FIG. 8 is a side perspective view of a medicament cartridge useful in the device of FIG. 1.

Any known medicament cartridge suitable for storing the medicament to be used and capable of interacting with piston 17 to expel medicament may be useful with the device of the invention. Preferably, the medicament cartridge is a compact cartridge holding about 200 to about 300 units of medicament, which medicament preferably is insulin. For example, as shown in FIG. 8, cartridge 30 includes plunger 31 therein. One end of the cartridge, the infusion end, is suitable for connecting to a cannula, needle or the like for infusion of the substance into the user. As shown, infusion end 32 includes a threaded fitting suitable for, for example, connecting to a conventional luer-type connection. However, any suitable connection may be used for infusion end 32.

Figure 9:
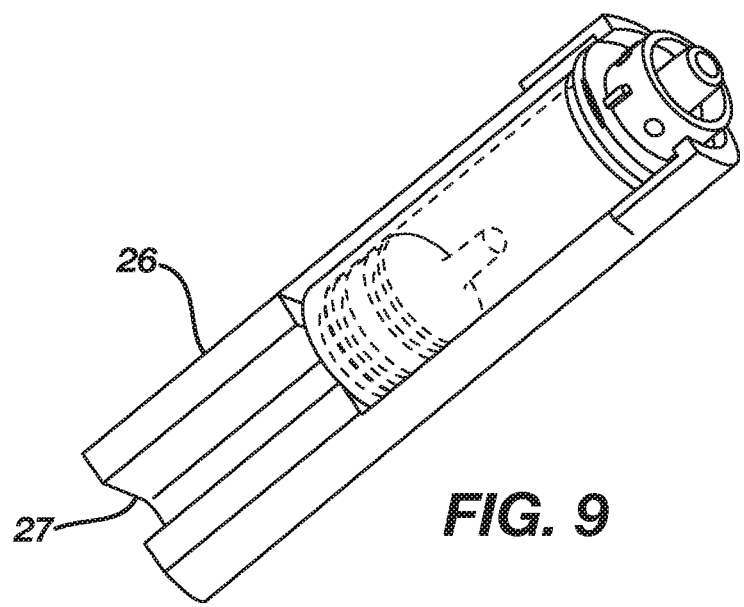
FIG. 9 is a side perspective view of cartridge of FIG. 8 in a cartridge retainer.
Figure 10:
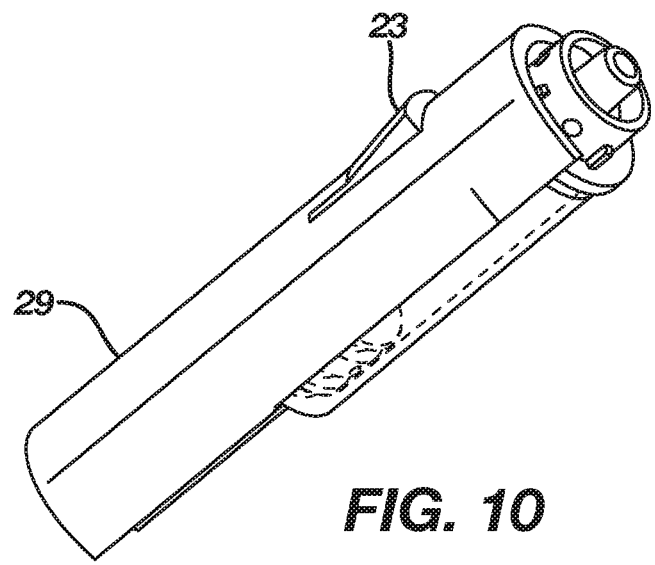
FIG. 10 is a side perspective view of the bottom surface of the cartridge retainer of FIG. 9.
Figure 11:
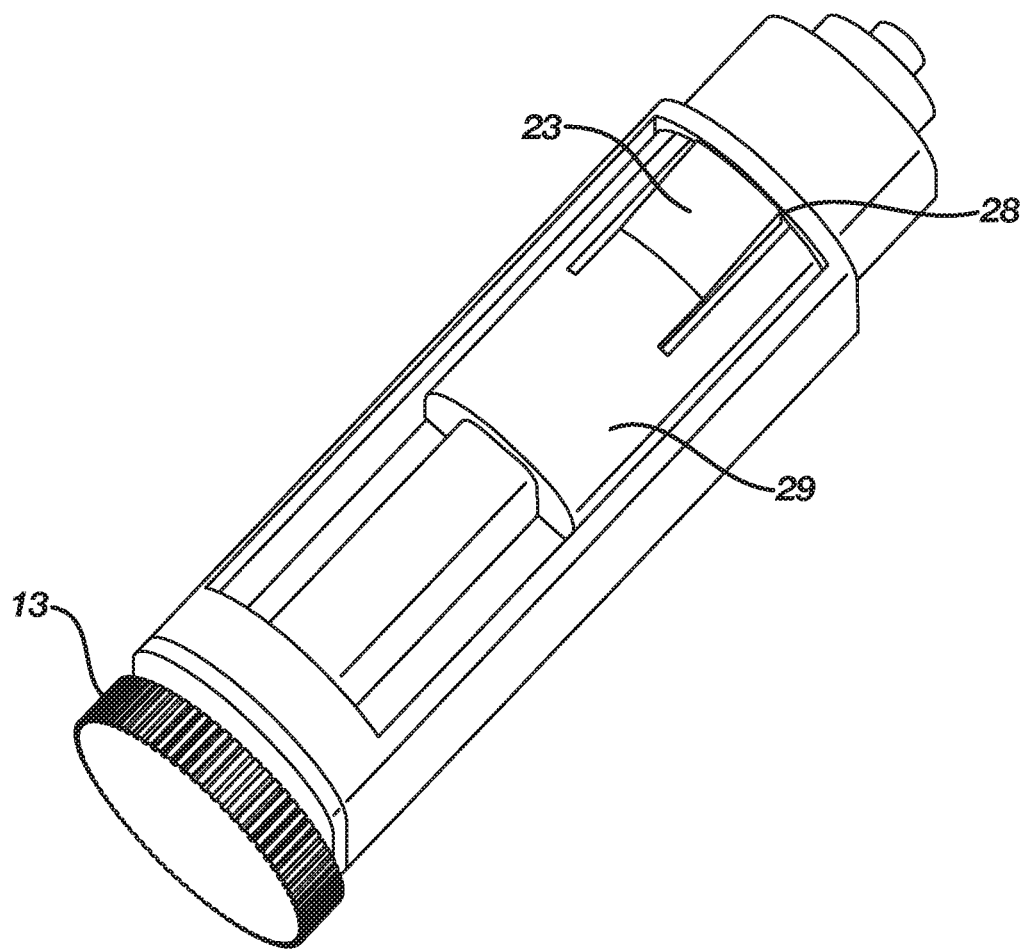
FIG. 11 is a top perspective view of the device of FIG. 1 with a portion of the housing and the display removed.

As shown in FIGS. 9, 10 and 11, within housing 11 is retainer 26 for holding cartridge 30 within the device. FIG. 11 depicts cartridge 30 assembled in retainer 26 within housing 11. As shown, retainer 26 is sized and shaped so that cartridge 30 may nest within one end of retainer 26 (FIGS. 9 and 10) and piston 17 nests in an opposite end (FIG. 11). Retainer 26 prevents piston 17 from rotating in response to leadscrew shaft 25 being rotated by the gearing interaction of gear 24 with leadscrew base 16. Snap 23, which is a flange integral with and extending from bottom surface 29 of retainer 26, abuts surface 28 of housing 11 against which it is held. Depression of snap 23 allows retainer 26 to pass under surface 28 and permits its removal from, or insertion into, the housing along with cartridge 30. Channel 27 within retainer 26, shown in FIG. 9, provides for access to plunger 31 by piston 17 and piston end 18. As piston 17 is extended by manual turning of wheel 13 and indexes along threaded shaft 25 and through channel 27 forcing piston end 18 to move plunger 31 resulting in expulsion of medicament from cartridge 30. Piston 17 is shown with piston end 18 engaged with plunger 31 in FIG. 11.

Figure 12:
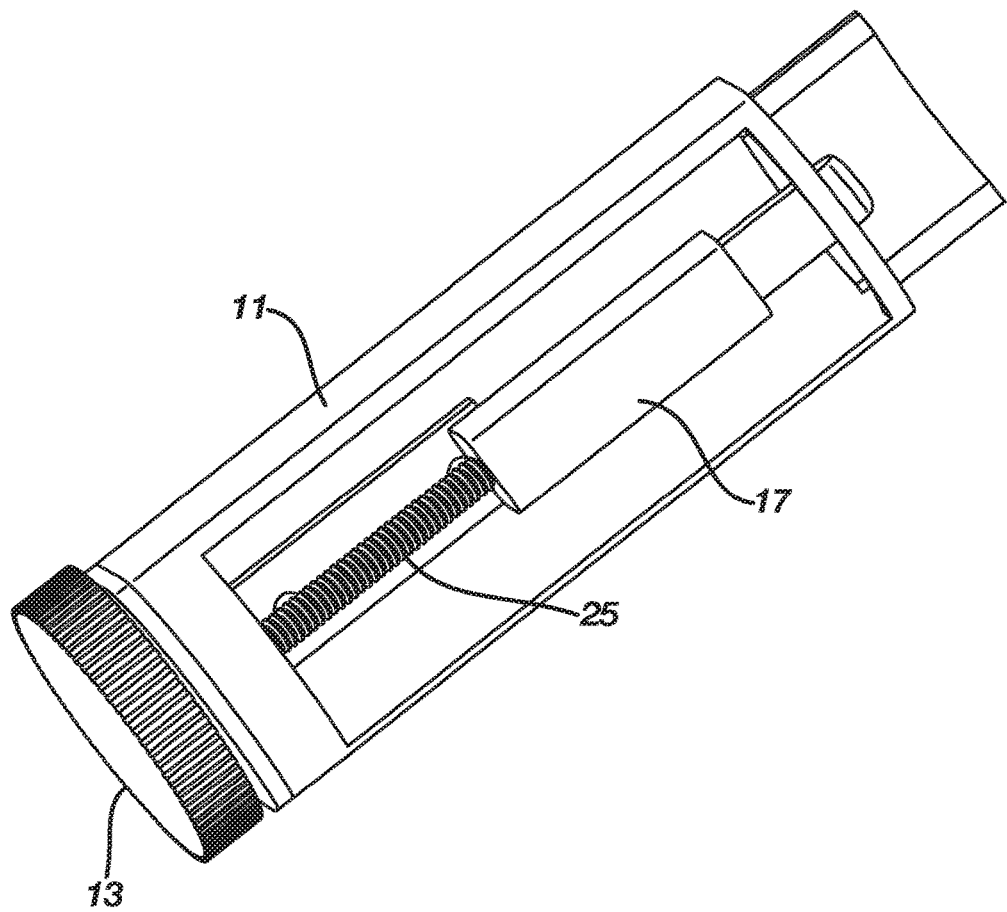
FIG. 12 is a top perspective view of the device of FIG. 1 with a portion of the housing and components removed to show the leadscrew shaft and piston at full extension.
Figure 13:
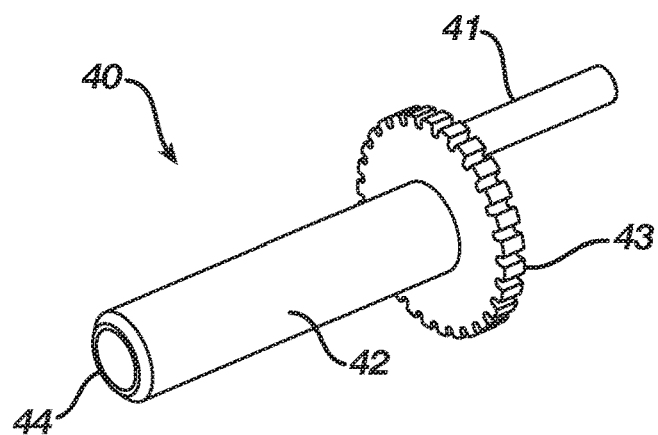
FIG. 13 is a side perspective view of a rewind tool useful with the device of FIG. 1.
Figure 14:
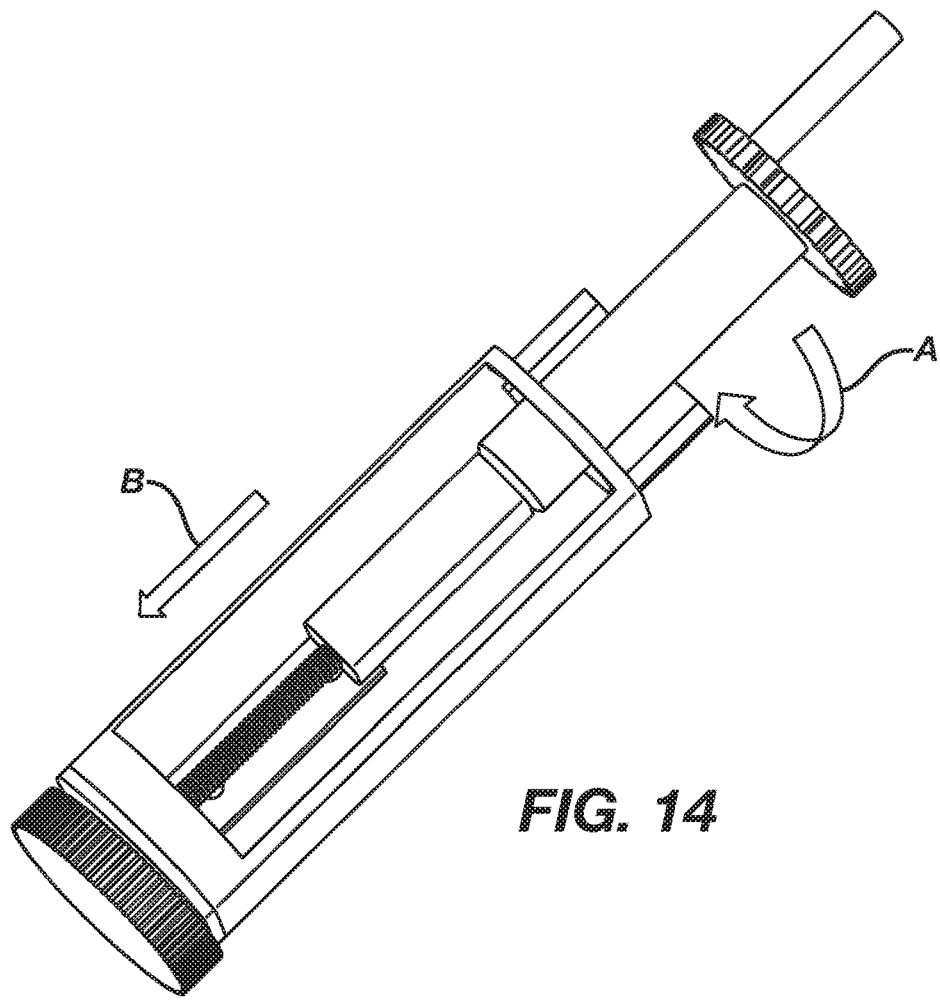
FIG. 14 is a view of the rewind tool of FIG. 13 shown in use with the device of FIG. 12.

One feature of the device of the invention is the ability to manually rewind the piston on the leadscrew enabling reuse of the device once the medicament cartridge is empty. FIG. 12 depicts housing 11 with an empty medicament cartridge and its retainer removed from the device and piston 17 is shown in its fully extended position along leadscrew shaft 25. If manual returning of piston 17 to its retracted start position within the device was performed against the gearing mechanism, hundreds of turns of the piston would be required to overcome the gearing ratio and index the piston to its original position. With the device of the invention, removal of the retainer and use of a rewind tool 40, shown in FIGS. 13 and 14, can be used to easily rewind the piston to its starting position. After cartridge 30 is emptied, retainer 26 along with the empty cartridge 30, are removed from the device. Removal of retainer 26 allows for rotation of piston 17. Rewind tool 40 includes turn handle 41, wheel 43 that preferably is grooved, indented or the like therearound to facilitate gripping, shaft 42 and opening 44. Opening 44 is sized and shaped to releasably engage piston end 18. FIG. 14 shows the rewind tool seated on the piston end. As the tool is turned in a clockwise direction, the piston rotates in a direction shown by arrow A resulting in indexing of the piston along shaft 25 in the direction indicated by arrow B.

The device of the invention may be worn by an individual on a belt, in a pocket of other suitable clothing compartment. Thus, additionally a removable adhesive pad may be provided to removably affix the device to the user's body. Preferably, the device is compact and sized and shaped to be unobtrusively worn and is between about 2.8×0.1.0.×0.9 inches to about 3.5×1.7×1.6 inches.

Figure 15A:
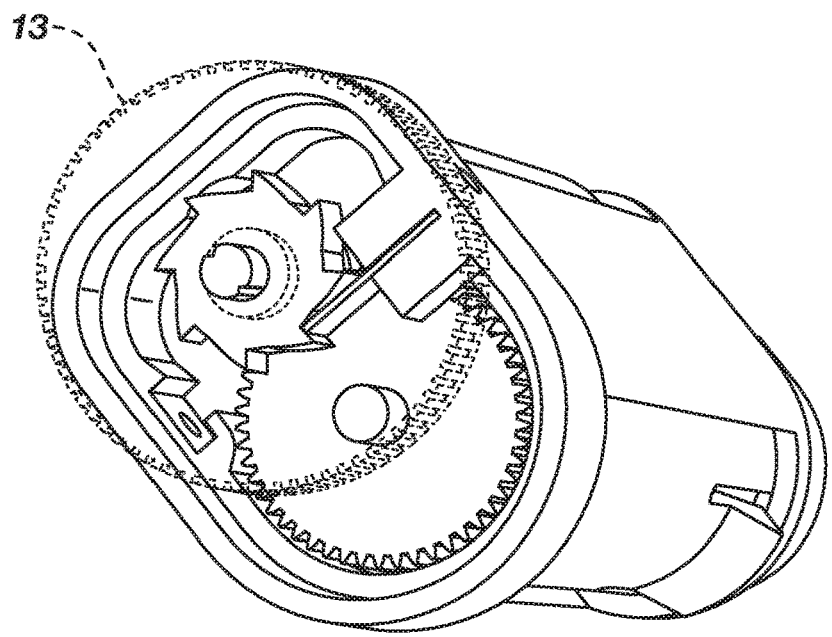
FIGS. 15A and 15B are perspective views of a locking mechanism for the device of FIG. 1.
Figure 15B:
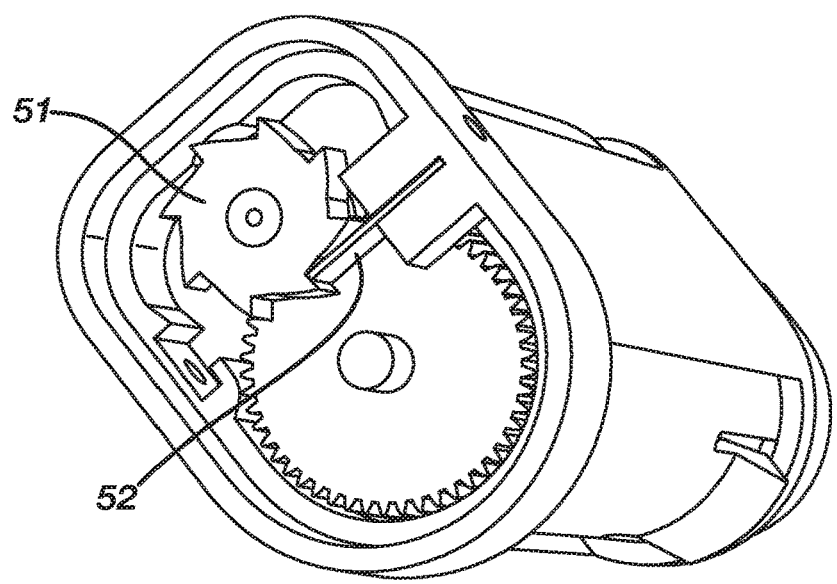

In one embodiment, a suitable locking mechanism that prevents the inadvertent forward indexing of piston 17 may be used. For example, and as shown in FIGS. 15A and 15B, a ratchet 51 may be mounted on drive wheel 13. In FIG. 15A, drive wheel 13 is shown in dotted line form and positioned so that ratchet 51 lies underneath it. Ratchet 51 cannot turn unless sufficient force is imposed by the device user on drive wheel 13 for the teeth of ratchet 51 to push past pawl 52, permitting rotation of the drive wheel and ultimately, medicament dispensing. Pawl 52 is of sufficient stiffness so that ratchet 51 cannot be turned in the non-dispensing direction. Because sufficient force is needed to overcome pawl 52, inadvertent turning of drive wheel 13, and thus inadvertent medicament dispensing, is prevented. A secondary advantage of the ratchet-pawl mechanism is the tactile feel the user experiences in turning drive wheel 13. When turned, every time pawl 52 is over-ridden by one of the ratchet's teeth, a snap and will be felt through drive wheel 13 to the user's hand. As yet another advantage, each snap will correspond to a set amount of turn and medicament being dispensed.

Alternatively, methods for completely locking drive wheel 13 may be used. Such methods may use a resilient, force loaded component, such as a pin to engage a corresponding hole in drive wheel 13. The user would pull the pin out to enable turning of the wheel.

In another embodiment, visual, audible or vibratory alarms may be added. Visual alarms could be provided via the indication device. Audible alarms may be provided through a speaker included within the device. A vibratory motor may be used to provide vibratory alarms to the user. The alarms may be used in combination, in escalating frequency, volume or the like or combinations thereof. The circuitry for such alarms and speaker may be incorporated onto the circuit board 24.

In yet other embodiments, a transmitter may be provided to transmit data, alarms or both to another device such as phone, computer, server, cloud or the like. Suitable transmitters for incorporation into such a pump are well known. Preferably, the transmitter is a BlueTooth® low energy transmitter.

It will be apparent that other modifications and variations of the device described are possible within the scope of the described invention. To the extent there are variations of the invention, which are within the spirit of the disclosure or equivalent to the inventions found in the claims, it is the intent these variations are covered as well herein.

What is claimed is:

1. A medicament infusion device comprising:
   a.) a housing;
   b.) a battery-operated indication device within the housing, wherein the indication device provides information about a medicament in a medicament cartridge;
   c.) a manually operated gearing mechanism consisting essentially of a manually operated drive wheel, a leadscrew base and a leadscrew shaft extending from the leadscrew base;
   d.) a piston comprising a piston end, wherein the piston is indexed in a first direction along the leadscrew shaft in response to turning of the manually operated drive wheel;
   e.) the medicament cartridge having a plunger therein that is engaged by the piston end;
   f.) a removable retainer for retaining the medicament cartridge and piston therein; and
   g.) a sensing mechanism for sensing a position of the piston on the leadscrew shaft.

2. The infusion device of claim 1, further comprising a rewind tool for returning the piston to an initial position on the leadscrew shaft.

3. The infusion device of claim 1, further comprising a ratchet and pawl capable of preventing inadvertent turning of the manually operated drive wheel.

4. The infusion device of claim 1, further comprising an adhesive pad on a surface of the housing for adhering the infusion device to a body of a device user.

* * * * *